(12) United States Patent
Olsen et al.

(10) Patent No.: US 11,999,948 B2
(45) Date of Patent: Jun. 4, 2024

(54) METHODS OF PRODUCING SIZE-SELECTED NUCLEIC ACID LIBRARIES AND COMPOSITIONS AND KITS FOR PRACTICING SAME

(71) Applicant: The Regents of the University of California, Oakland, CA (US)

(72) Inventors: Hugh E. Olsen, Davis, CA (US); Miten Jain, Santa Cruz, CA (US); Mark A. Akeson, Santa Cruz, CA (US)

(73) Assignee: The Regents of the University of California, Oakland, CA (US)

( * ) Notice: Subject to any disclaimer, the term of this patent is extended or adjusted under 35 U.S.C. 154(b) by 448 days.

(21) Appl. No.: 15/970,690

(22) Filed: May 3, 2018

(65) Prior Publication Data
US 2018/0320168 A1 Nov. 8, 2018

Related U.S. Application Data

(60) Provisional application No. 62/501,578, filed on May 4, 2017.

(51) Int. Cl.
| | |
|---|---|
| C12Q 1/6809 | (2018.01) |
| C12N 15/10 | (2006.01) |
| C12N 15/11 | (2006.01) |
| C12Q 1/6806 | (2018.01) |
| C40B 30/04 | (2006.01) |
| C40B 70/00 | (2006.01) |
| C40B 40/06 | (2006.01) |

(52) U.S. Cl.
CPC ..... *C12N 15/1065* (2013.01); *C12N 15/1068* (2013.01); *C12N 15/1093* (2013.01); *C12N 15/11* (2013.01); *C12Q 1/6806* (2013.01); *C40B 30/04* (2013.01); *C40B 70/00* (2013.01); *B01J 2219/00454* (2013.01); *B01J 2219/005* (2013.01); *B01J 2219/00677* (2013.01); *B01J 2219/00722* (2013.01); *B01J 2219/00759* (2013.01); *C40B 40/06* (2013.01)

(58) Field of Classification Search
CPC .................................................. C12N 15/10
See application file for complete search history.

(56) References Cited

U.S. PATENT DOCUMENTS

| | | | | |
|---|---|---|---|---|
| 2014/0255921 A1* | 9/2014 | Moysey | ............... | C12Q 1/6869 435/6.1 |
| 2015/0360194 A1* | 12/2015 | Bustamante | ....... | C12N 15/1006 506/2 |
| 2016/0304829 A1* | 10/2016 | Neurauter | ............ | G01N 33/543 |

FOREIGN PATENT DOCUMENTS

WO    WO-2016065300 A1 * 4/2016 ........... B01L 3/5027

OTHER PUBLICATIONS

Dhaliwal, A., DNA Extraction and Purification, Labome, 2013, 1-27. (Year: 2013).*
Spisak et al., Complete Genes May Pass From Food to Human Blood, PLoS One, 2013, 8(7), 1-11. (Year: 2013).*
Ku et al., From Next-Generation Sequencing to Nanopore Sequencing Technology: Paving The Way to Personalized Genomic Medicine, Expert Reviews of Medical Devices, 2014, 10(1)-1-6. (Year: 2014).*
Islam et al., Comparisons of Direct Extraction Methods of Microbial DNA from Different Paddy Soils, Saudi Journal of Biological Sciences, 2012, 19, 337-342. (Year: 2012).*
Nayfach et al., Average Genome Size Estimation Improves Comparative Metagenomics and Sheds Light on the Functional Ecology of the Human Microbiome, Genome Biology, 2015, 16(51), 1-18. (Year: 2015).*
(Feb. 11, 2016) "MagSi-NGSPREP Plus" AMSBIO, Product Manuel, Version 1.1, 13 pgs.
Luck et al. (2017) "Removing the needle from the haystack: Enrichment of Wolbachia endosymbiont transcripts from host nematode RNA by Cappable-seq™" PLoS ONE, 12(3):e0173186.
Škopić et al. (2016) "Design and synthesis of DNA-encoded libraries based on a benzodiazepine and a byrazolopyrimidine scaffold" Med. Chem. Commun, 7:1957-1965.

* cited by examiner

*Primary Examiner* — Amy M Bunker
(74) *Attorney, Agent, or Firm* — Brian E. Davy; Bozicevic, Field & Francis LLP

(57) ABSTRACT

Provided are methods of producing size-selected nucleic acid libraries. The methods include contacting a nucleic acid sample and a nucleic acid binding reagent including an affinity tag, under conditions in which nucleic acids of less than a desired length are substantially bound to the nucleic acid binding reagent and nucleic acids of the desired length are substantially not bound to the nucleic acid binding reagent. The conditions include the duration of the contacting, the concentration of the nucleic acid binding reagent, or both. The methods further include separating, using the affinity tag, the nucleic acids of less than the desired length bound to the nucleic acid binding reagent from the nucleic acids of the desired length not bound to the nucleic acid binding reagent, to produce a size-selected nucleic acid library. Compositions and kits that find use, e.g., in practicing the methods of the present disclosure, are also provided.

11 Claims, 2 Drawing Sheets
Specification includes a Sequence Listing.

METHODS OF PRODUCING SIZE-SELECTED NUCLEIC ACID LIBRARIES AND COMPOSITIONS AND KITS FOR PRACTICING SAME

CROSS-REFERENCE TO RELATED APPLICATIONS

This application claims the benefit of U.S. Provisional Patent Application No. 62/501,578, filed May 4, 2017, which application is incorporated herein by reference in its entirety.

STATEMENT REGARDING FEDERALLY SPONSORED RESEARCH

This invention was made with Government support under Grant No. HG007827, awarded by the National Institutes of Health. The Government has certain rights in the invention.

INCORPORATION BY REFERENCE OF SEQUENCE LISTING PROVIDED AS A SEQUENCE LISTING XML FILE

A Sequence Listing is provided herewith in a text file, UCSC-358_SEQ_LIST, created on Mar. 18, 2024 and having a size of 836 bytes. The contents of the text file are incorporated herein by reference in their entirety.

INTRODUCTION

Recent advances in DNA sequencing have revolutionized the field of genomics, making it possible for even single research groups to generate large amounts of sequence data very rapidly and at a substantially lower cost. These high-throughput sequencing technologies make deep transcriptome sequencing and transcript quantification, whole genome sequencing and resequencing available to many more researchers and projects.

A variety of commercial high-throughput sequencing platforms exist and are described, e.g., in Metzker, M. L. (2010) *Nat. Rev. Genet.* 11:31-46, Morey et al. (2013) *Mol. Genet. Metab.* 110: 3-24, Reuter et al. (2015) *Molecular Cell* 58(4):586-597, and elsewhere. In the Illumina platform, the sequencing process involves clonal amplification of adaptor-ligated DNA fragments on the surface of a glass slide. Bases are read using a cyclic reversible termination strategy, which sequences the template strand one nucleotide at a time through progressive rounds of base incorporation, washing, imaging, and cleavage. In this strategy, fluorescently labeled 3'-O-azidomethyl-dNTPs are used to pause the polymerization reaction, enabling removal of unincorporated bases and fluorescent imaging to determine the added nucleotide. Following scanning of the flow cell with a coupled-charge device (CCD) camera, the fluorescent moiety and the 3' block are removed, and the process is repeated.

An emerging single-molecule strategy that has made significant progress in recent years is nanopore-based sequencing. Nanopore sequencing principally relies on the transition of DNA, RNA, or individual nucleotides through a small channel. A sequencing flow cell includes independent micro-wells, each containing a synthetic bilayer perforated by nanopores. Sequencing is accomplished by measuring characteristic changes in current that are induced as the bases are threaded through the pore by a molecular motor protein. Library preparation is minimal, involving fragmentation of DNA and ligation of adapters, and can be done with or without PCR amplification. The library design allows sequencing of both strands of DNA from a single molecule, which increases accuracy.

A difficulty in long sequencing reads of genomic DNA is delivery of only properly adapted un-sheared long (>100 kb) DNA to the DNA sequencer. The presence of shorter DNA strands reduces throughput for the desired long strand reads. One of the challenges in this process is removing unwanted shorter DNA strands in the sequencing library. Size selection may be accomplished with expensive and time-consuming methodologies (e.g. the BluePippin™ DNA Size Selection System available from Sage Science), which also require relatively large microgram quantities of DNA. Simpler, rapid and less expensive methods for size selection are needed.

SUMMARY

Provided are methods of producing size-selected nucleic acid libraries. In certain aspects, the methods include contacting a nucleic acid sample and a nucleic acid binding reagent including an affinity tag, under conditions in which nucleic acids of less than a desired length are substantially bound to the nucleic acid binding reagent and nucleic acids of the desired length are substantially not bound to the nucleic acid binding reagent. The conditions include the duration of the contacting, the concentration of the nucleic acid binding reagent, or both. The methods further include separating, using the affinity tag, the nucleic acids of less than the desired length bound to the nucleic acid binding reagent from the nucleic acids of the desired length not bound to the nucleic acid binding reagent, to produce a size-selected nucleic acid library. Kits that find use, e.g., in practicing the methods of the present disclosure, are also provided.

DETAILED DESCRIPTION

Figure 1:
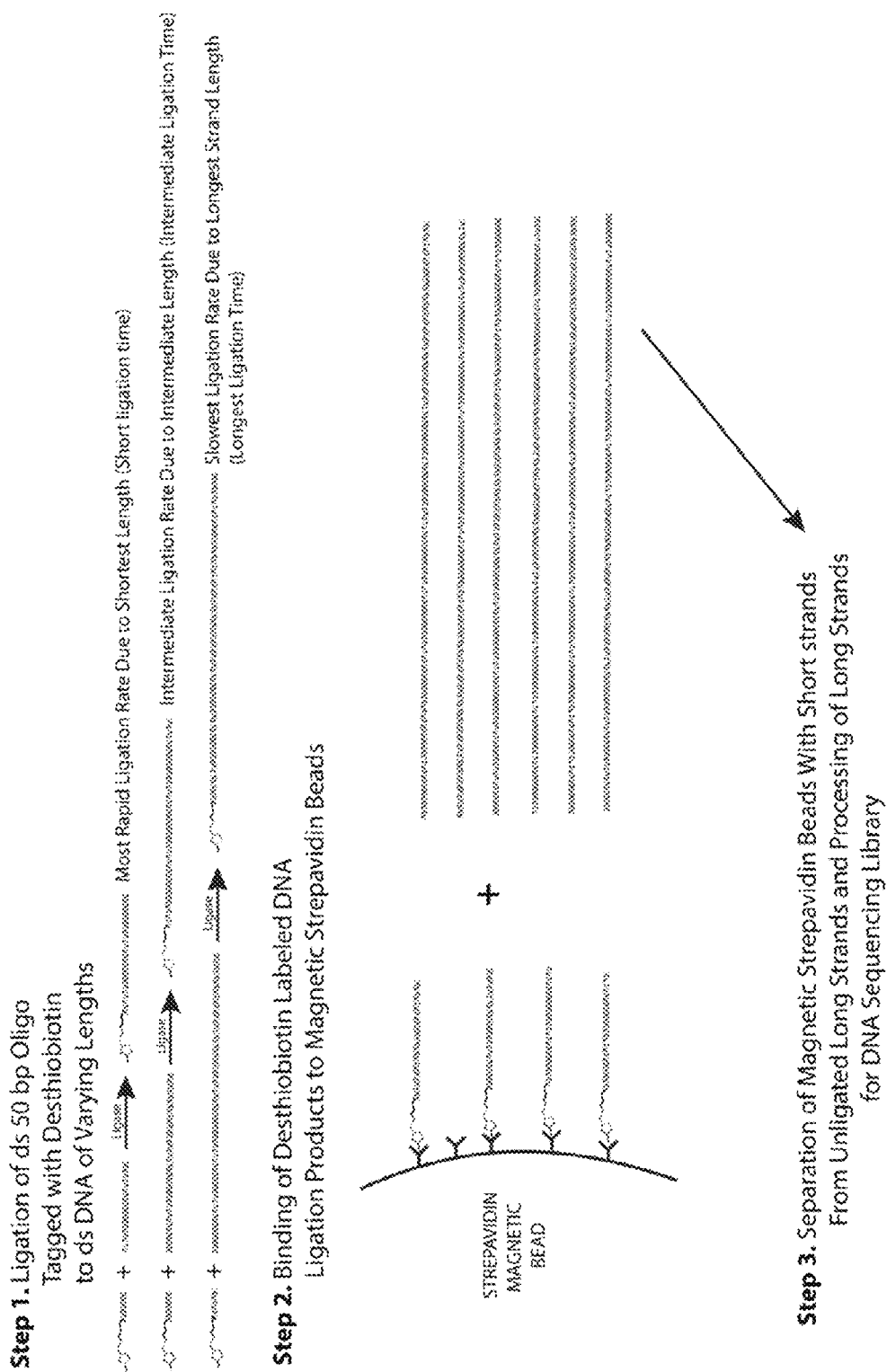
FIG. 1 schematically illustrates an example method of producing a size-selected nucleic acid library according to one embodiment of the present disclosure.

Provided are methods of producing size-selected nucleic acid libraries. In certain aspects, the methods include contacting a nucleic acid sample and a nucleic acid binding reagent including an affinity tag, under conditions in which nucleic acids of less than a desired length are substantially bound to the nucleic acid binding reagent and nucleic acids of the desired length are substantially not bound to the nucleic acid binding reagent. The conditions include the duration of the contacting, the concentration of the nucleic acid binding reagent, or both. The methods further include separating, using the affinity tag, the nucleic acids of less than the desired length bound to the nucleic acid binding reagent from the nucleic acids of the desired length not bound to the nucleic acid binding reagent, to produce a size-selected nucleic acid library. Kits that find use, e.g., in practicing the methods of the present disclosure, are also provided.

Before the methods, compositions and kits of the present disclosure are described in greater detail, it is to be understood that the methods, compositions and kits are not limited to particular embodiments described, as such may, of course, vary. It is also to be understood that the terminology used herein is for the purpose of describing particular embodiments only, and is not intended to be limiting, since the scope of the methods, compositions and kits will be limited only by the appended claims.

Where a range of values is provided, it is understood that each intervening value, to the tenth of the unit of the lower limit unless the context clearly dictates otherwise, between the upper and lower limit of that range and any other stated or intervening value in that stated range, is encompassed within the methods, compositions and kits. The upper and lower limits of these smaller ranges may independently be included in the smaller ranges and are also encompassed within the methods, compositions and kits, subject to any specifically excluded limit in the stated range. Where the stated range includes one or both of the limits, ranges excluding either or both of those included limits are also included in the methods, compositions and kits.

Certain ranges are presented herein with numerical values being preceded by the term "about." The term "about" is used herein to provide literal support for the exact number that it precedes, as well as a number that is near to or approximately the number that the term precedes. In determining whether a number is near to or approximately a specifically recited number, the near or approximating unrecited number may be a number which, in the context in which it is presented, provides the substantial equivalent of the specifically recited number.

Unless defined otherwise, all technical and scientific terms used herein have the same meaning as commonly understood by one of ordinary skill in the art to which the methods, compositions and kits belong. Although any methods, compositions and kits similar or equivalent to those described herein can also be used in the practice or testing of the methods, compositions and kits, representative illustrative methods, compositions and kits are now described.

All publications and patents cited in this specification are herein incorporated by reference as if each individual publication or patent were specifically and individually indicated to be incorporated by reference and are incorporated herein by reference to disclose and describe the materials and/or methods in connection with which the publications are cited. The citation of any publication is for its disclosure prior to the filing date and should not be construed as an admission that the present methods, compositions and kits are not entitled to antedate such publication, as the date of publication provided may be different from the actual publication date which may need to be independently confirmed.

It is noted that, as used herein and in the appended claims, the singular forms "a", "an", and "the" include plural referents unless the context clearly dictates otherwise. It is further noted that the claims may be drafted to exclude any optional element. As such, this statement is intended to serve as antecedent basis for use of such exclusive terminology as "solely," "only" and the like in connection with the recitation of claim elements, or use of a "negative" limitation.

It is appreciated that certain features of the methods, compositions and kits, which are, for clarity, described in the context of separate embodiments, may also be provided in combination in a single embodiment. Conversely, various features of the methods, compositions and kits, which are, for brevity, described in the context of a single embodiment, may also be provided separately or in any suitable sub-combination. All combinations of the embodiments are specifically embraced by the present disclosure and are disclosed herein just as if each and every combination was individually and explicitly disclosed, to the extent that such combinations embrace operable processes and/or compositions. In addition, all sub-combinations listed in the embodiments describing such variables are also specifically embraced by the present methods, compositions and kits and are disclosed herein just as if each and every such sub-combination was individually and explicitly disclosed herein.

As will be apparent to those of skill in the art upon reading this disclosure, each of the individual embodiments described and illustrated herein has discrete components and features which may be readily separated from or combined with the features of any of the other several embodiments without departing from the scope or spirit of the present methods. Any recited method can be carried out in the order of events recited or in any other order that is logically possible.

Methods

As summarized above, the present disclosure provides methods of producing size-selected nucleic acid libraries. In certain aspects, the methods include contacting a nucleic acid sample and a nucleic acid binding reagent including an affinity tag, under conditions in which nucleic acids of less than a desired length are substantially bound to the nucleic acid binding reagent and nucleic acids of the desired length are substantially not bound to the nucleic acid binding reagent. The conditions include the duration of the contacting, the concentration of the nucleic acid binding reagent, or both. The methods further include separating, using the affinity tag, the nucleic acids of less than the desired length bound to the nucleic acid binding reagent from the nucleic acids of the desired length not bound to the nucleic acid binding reagent, to produce a size-selected nucleic acid library.

The nucleic acid sample (e.g., a genomic DNA sample, a mitochondrial DNA sample, an RNA sample, or the like) contacted with the nucleic acid binding reagent may be any nucleic acid sample of interest, including but not limited to, a nucleic acid sample isolated from a single cell, a plurality of cells (e.g., cultured cells), a tissue, an organ, or an organism (e.g., bacteria, yeast, or the like). In certain aspects, the nucleic acid sample is isolated from a cell(s), tissue, organ, and/or the like of an animal. In some embodiments, the animal is a mammal (e.g., a mammal from the genus Homo, a rodent (e.g., a mouse or rat), a dog, a cat, a horse, a cow, or any other mammal of interest). In other aspects, the nucleic acid sample is isolated/obtained from a source other than a mammal, such as bacteria, yeast, insects (e.g., *drosophila*), amphibians (e.g., frogs (e.g., *Xenopus*)), viruses, plants, or any other non-mammalian nucleic acid sample source.

In certain aspects, the nucleic acid sample is a tumor nucleic acid sample (that is, a nucleic acid sample isolated from a tumor). As used herein, "tumor" refers to all neoplastic cell growth and proliferation, whether malignant or benign, and all pre-cancerous and cancerous cells and tissues. The terms "cancer" and "cancerous" refer to or describe the physiological condition in mammals that is typically characterized by unregulated cell growth/proliferation. Examples of cancer include but are not limited to, carcinoma, lymphoma, blastoma, sarcoma, and leukemia. More particular examples of such cancers include squamous cell cancer, small-cell lung cancer, non-small cell lung cancer, adenocarcinoma of the lung, squamous carcinoma of the lung, cancer of the peritoneum, hepatocellular cancer, gastrointestinal cancer, pancreatic cancer, glioblastoma, cervical cancer, ovarian cancer, liver cancer, bladder cancer, hepatoma, breast cancer, colon cancer, colorectal cancer, endometrial or uterine carcinoma, salivary gland carcinoma, kidney cancer, liver cancer, prostate cancer, vulval cancer, thyroid cancer, hepatic carcinoma, various types of head and neck cancer, and the like.

According to certain embodiments, the nucleic acid sample is a cell-free nucleic acid sample (e.g., cell-free DNA, cell-free RNA, or both). Such cell-free nucleic acids may be obtained from any suitable source. In certain aspects, the cell-free nucleic acids are obtained from a body fluid sample selected from the group consisting of: whole blood, blood plasma, blood serum, amniotic fluid, saliva, urine, pleural effusion, bronchial lavage, bronchial aspirates, breast milk, colostrum, tears, seminal fluid, peritoneal fluid, pleural effusion, and stool. In some embodiments, the cell-free nucleic acids are cell-free fetal DNAs. In certain aspects, the cell-free nucleic acids are circulating tumor DNAs.

In some embodiments, the nucleic acid sample is obtained (e.g., isolated from) an environmental sample. In some embodiments, the environmental sample is a liquid environmental sample. The liquid environmental sample may be, e.g., drinking (or potable) water, surface water (e.g., river water, stream water, lake water, reservoir water, wetland water, bog water, or the like), ground water, waste water, well water, water from an unsaturated zone, rain water, run-off water, sea water, liquid industrial waste, sewage, surface films, or the like. In certain aspects, the environmental sample is a solid environmental sample. The solid environmental sample may be, e.g., ice, snow, soil, sewage sludge, bottom sediments, dust from electrofilters, vacuuming dust, plant material, forest floor, industrial waste, municipal waste, ashes, or the like.

Approaches, reagents and kits for isolating DNA and RNA from sources of interest are known in the art and commercially available. For example, kits for isolating DNA from a source of interest include the DNeasy®, RNeasy®, QIAamp®, QIAprep® and QIAquick® nucleic acid isolation/purification kits by Qiagen, Inc. (Germantown, Md); the DNAzol®, ChargeSwitch®, Purelink®, GeneCatcher® nucleic acid isolation/purification kits by Life Technologies, Inc. (Carlsbad, CA); the NucleoMag®, NucleoSpin®, and NucleoBond® nucleic acid isolation/purification kits by Clontech Laboratories, Inc. (Mountain View, CA). In certain aspects, the nucleic acid is isolated from a fixed biological sample, e.g., formalin-fixed, paraffin-embedded (FFPE) tissue. Genomic DNA from FFPE tissue may be isolated using commercially available kits—such as the AllPrep® DNA/RNA FFPE kit by Qiagen, Inc. (Germantown, Md), the RecoverAll® Total Nucleic Acid Isolation kit for FFPE by Life Technologies, Inc. (Carlsbad, CA), and the NucleoSpin® FFPE kits by Clontech Laboratories, Inc. (Mountain View, CA).

In some embodiments, the nucleic acid sample is a deoxyribonucleic acid (DNA) sample. The DNA sample may be, e.g., a genomic DNA sample. In certain aspects, the nucleic acid sample is a mitochondrial DNA sample. The DNA sample may include both genomic DNA and mitochondrial DNA. In some embodiments, the DNA sample is a complementary DNA (cDNA) sample, e.g., produced from messenger RNA (mRNA). Reagents and kits for carrying out such reverse transcription are readily available and include, e.g., the SuperScript IV First-Strand Synthesis System available from Thermo Fisher Scientific.

As summarized above, the contacting step is carried out under conditions in which nucleic acids of less than a desired length are substantially bound to the nucleic acid binding reagent and nucleic acids of the desired length are substantially not bound to the nucleic acid binding reagent. The present disclosure is based in part on the inventors' observations that the attachment of sequencing adapters (e.g., by enzymatic ligation) to nucleic acids in a nucleic acid sample of interest is much more rapid for short double-stranded DNA than for longer double-stranded DNA. The short strands were interfering with preparation of long strand DNA sequencing libraries and collection of data for long DNA strands. Based on this observation, the inventors discovered that attachment of a nucleic acid binding reagent that includes an affinity tag (e.g., ligation of an oligonucleotide labeled with, e.g., desthiobiotin) selectively to short strands permits size-selection of larger strands for a downstream application of interest, e.g., nucleic acid sequencing.

The conditions in which nucleic acids of less than a desired length are substantially bound to the nucleic acid binding reagent and nucleic acids of the desired length are substantially not bound to the nucleic acid binding reagent include the duration of the contacting, the concentration of the nucleic acid binding reagent, or both. In some embodiments, the conditions consist of the duration of the contacting. In other embodiments, the conditions consist of the concentration of the nucleic acid binding reagent. In still other embodiments, the conditions consist of the duration of the contacting and the concentration of the nucleic acid binding reagent.

When the conditions include, or consist of, the duration of the contacting, a shorter duration reduces the probability of longer nucleic acids being bound to the nucleic acid binding reagent, thereby increasing the proportion of longer nucleic acids in the size-selected nucleic acid library. Conversely, a longer duration increases the probability of longer nucleic acids being bound to the nucleic acid binding reagent. Suitable durations will vary depending upon the desired length of the size-selected library, and a suitable duration may be determined without undue experimentation, e.g., by gel electrophoresis (e.g., pulsed field gel electrophoresis), or the like, to determine a duration for which nucleic acids of less than the desired length are substantially bound to the nucleic acid binding reagent and nucleic acids of the desired length are substantially not bound to the nucleic acid binding reagent.

The conditions (e.g., including or consisting of the duration of the contacting, the concentration of the nucleic acid binding reagent, or both) are such that a percentage of the nucleic acids of less than the desired length are bound to the nucleic acid binding reagent during the separating. In some embodiments, the conditions are such that 20% or more, 25% or more, 30% or more, 35% or more, 40% or more, 50% or more, 55% or more, 60% or more, 65% or more, 70% or more, 75% or more, 80% or more, 85% or more, 90% or more, 95% or more, or 99% or more, of the nucleic acids of less than the desired length are bound to the nucleic acid binding reagent during the separating.

The conditions (e.g., including or consisting of the duration of the contacting, the concentration of the nucleic acid binding reagent, or both) are such that a percentage of the nucleic acids of the desired length are not bound to the nucleic acid binding reagent during the separating. In certain aspects, the conditions are such that 20% or more, 25% or more, 30% or more, 35% or more, 40% or more, 50% or more, 55% or more, 60% or more, 65% or more, 70% or more, 75% or more, 80% or more, 85% or more, 90% or more, 95% or more, or 99% or more, of the nucleic acids of the desired length are not bound to the nucleic acid binding reagent during the separating.

In certain aspects, the nucleic acid sample includes genomic DNA, and the nucleic acids (e.g., genomic DNA) of the desired length are 10 kilobases (kb) or greater, 20 kb or greater, 25 kb or greater, 30 kb or greater, 40 kb or greater, 50 kb or greater, 60 kb or greater, 70 kb or greater, 80 kb or greater, 90 kb or greater, 100 kb or greater, 120 kb or greater, 140 kb or greater, 150 kb or greater, 160 kb or greater, 180 kb or greater, 200 kb or greater, 225 kb or greater, 250 kb or greater, 275 kb or greater, 300 kb or greater, 400 kb or greater, 500 kb or greater, 600 kb or greater, 700 kb or greater, 800 kb or greater, 900 kb or greater, or 1 Mb or greater, in length.

In some embodiments, the nucleic acid sample includes ribonucleic acid (RNA), complementary DNA (cDNA), or both, and the nucleic acids (e.g., mRNAs and/or cDNAs produced therefrom) of the desired length are 200 base pairs (bp) or greater, 300 bp or greater, 400 bp or greater, 500 bp or greater, 600 bp or greater, 700 bp or greater, 800 bp or greater, 900 bp or greater, 1 kb or greater, 1.5 kb or greater, 2.0 kb or greater, 2.5 kb or greater, 3.0 kb or greater, 3.5 kb or greater, 4.0 kb or greater, 4.5 kb or greater, 5.0 kb or greater, 5.5 kb or greater, 6.0 kb or greater, 6.5 kb or greater, 7.0 kb or greater, 7.5 kb or greater, 8.0 kb or greater, 8.5 kb or greater, 9.0 kb or greater, 9.5 kb or greater, or 10 kb or greater, in length.

Any suitable nucleic acid binding reagent may be employed. The nucleic acid binding reagent (e.g., a nucleic acid including an affinity tag) may be adapted to bind non-covalently (e.g., by hybridization) to nucleic acids in the nucleic acid sample. In other aspects, the nucleic acid binding reagent (e.g., a nucleic acid including an affinity tag) may be adapted to bind covalently to nucleic acids in the nucleic acid sample. Covalent binding may be by chemical attachment, enzymatic ligation, or the like.

In certain aspects, the nucleic acid binding reagent includes a nucleic acid. In some embodiments, when the nucleic acid binding reagent includes a nucleic acid, the nucleic acid of the nucleic acid binding reagent is an oligonucleotide. The oligonucleotide may be single-stranded, double-stranded, or include one or more single- and double-stranded regions. In certain aspects, the oligonucleotide includes a multimer of nucleotides from 5 to 500 nucleotides, e.g., 5 to 100 nucleotides. Oligonucleotides may be synthetic or may be made enzymatically, and, in some embodiments, are 5 to 75 nucleotides in length. Oligonucleotides may contain ribonucleotide monomers (i.e., may be oligoribonucleotides or "RNA oligonucleotides"), deoxyribonucleotide monomers (i.e., may be oligodeoxyribonucleotides or "DNA oligonucleotides"), or a combination thereof.

In some embodiments, the oligonucleotide is a double-stranded (or predominantly double-stranded) oligonucleotide having a length of 150 nucleotides or less, 125 nucleotides or less, 100 nucleotides or less, 90 nucleotides or less, 80 nucleotides or less, 70 nucleotides or less, 60 nucleotides or less, 50 nucleotides or less, 40 nucleotides or less, 30 nucleotides or less, 20 nucleotides or less, 10 nucleotides or less, or 5 nucleotides or less. In certain aspects, the oligonucleotide is a double-stranded (or predominantly double-stranded) oligonucleotide having a length of from 5 to 100 nucleotides, 10 to 80 nucleotides, 20 to 70 nucleotides, or 30 to 60 nucleotides (e.g., about 40 nucleotides, or about 50 nucleotides).

In some embodiments, when the nucleic acid binding reagent includes a nucleic acid, the nucleic acid of the nucleic acid binding reagent includes one or more non-natural nucleotides (which may also be referred to as nucleotide analogs). Non-limiting examples of non-natural nucleotides that may be included in the nucleic acid of the nucleic acid binding reagent are LNA (locked nucleic acid), PNA (peptide nucleic acid), FANA (2'-deoxy-2'-fluoroarabinonucleotide), GNA (glycol nucleic acid), TNA (threose nucleic acid), 2'-O-Me RNA, 2'-fluoro RNA, Morpholino nucleotides, and any combination thereof.

In some embodiments, when the nucleic acid binding reagent includes a nucleic acid, the nucleic acid of the nucleic acid binding reagent includes one or more universal bases. As used herein, a "universal base" is a base capable of indiscriminately base pairing with each of the four standard nucleotide bases: A, C, G and T. Universal bases that may be incorporated into the nucleic acid of the nucleic acid binding reagent include, but are not limited to, 2'-deoxyinosine (dI, dInosine) and 5-nitroindole.

As summarized above, the nucleic acid binding reagent includes an affinity tag. As used herein, the term "affinity tag" refers to a chemical moiety that functions as, or contains, an affinity ligand that is capable of binding (e.g., non-covalently or covalently) to a second, "capture" chemical moiety, such that the nucleic acid binding reagent (e.g., bound to a nucleic acid of less than the desired length) can be selected (or "captured") from a mixture using the capture moiety. In some embodiments, the capture moiety is bound to a solid support, e.g., a bead (e.g., a latex bead, a magnetic bead, or other suitable bead), planar surface, or the like. Non-limiting examples of affinity tags that may be included in the nucleic acid binding reagent (which may be, e.g., any of the oligonucleotides described herein) include biotin, a biotin analog (e.g., desthiobiotin, such as 5' desthiobiotin-TEG), avidin, streptavidin, an aptamer (see, e.g., Wilson & Szostak (1999) *Annu Rev Biochem.* 68:611-647), an MS2 coat protein-interacting sequence, a WA protein-interacting sequence, etc. Nucleic acid affinity tags that find use in the methods of the present disclosure are described, e.g., in Walker et al. (2008) *Methods Mol Biol.* 488:23-40. Interactions between the affinity tag and the capture moiety may be specific and reversible (e.g., non-covalent binding or hydrolyzable covalent linkage), but if desired, may be (or subsequently may be made) irreversible, e.g., a non-hydrolyzable covalent linkage between the affinity tag and the capture moiety.

Because of its especially high affinity and binding specificity, the biotin-avidin (or biotin-streptavidin) interaction has been used to label, detect and purify biomolecules. However, one limitation of the biotin-avidin interaction in purification applications is that it is essentially irreversible under physiological conditions. For example, once the biotinylated biomolecules in a sample are successfully captured by streptavidin agarose or magnetic beads, they cannot be dissociated (eluted and recovered) without using harsh conditions (boiling, extreme pH, or denaturants). These conditions tend to, e.g., denature proteins of interest, or cause artifacts in downstream applications, such as gel electrophoresis.

Desthiobiotin, a non-sulfur containing biotin analog, binds less tightly to avidin and streptavidin than biotin ($Kd=10^{-11}$ M versus $Kd=10^{-15}$ M, respectively) but nonetheless provides a high level of specificity. Unlike biotinylated biomolecules, desthiobiotinylated biomolecules can be readily and specifically eluted under mild conditions when captured on streptavidin by using biotin or a biotin elution buffer. The soft release characteristic of desthiobiotin minimizes the isolation of naturally biotinylated molecules that can interfere with results and also eliminates the use of harsh elution conditions which can disassociate complexes and/or damage the target biomolecules.

In certain aspects, when the nucleic acid binding reagent includes a nucleic acid, binding of nucleic acids of less than the desired length to the nucleic acid binding reagent includes covalently linking the nucleic acids of less than the desired length to the nucleic acid of the nucleic acid binding reagent. Such covalent linking may be, e.g., by chemical attachment, enzymatic ligation, or the like. Suitable reagents (e.g., ligases) and kits for performing enzymatic ligation reactions are known and available, e.g., the Instant Sticky-end Ligase Master Mix available from New England Biolabs (Ipswich, MA). Ligases that may be employed include, e.g., T4 DNA ligase (e.g., at low or high concentration), T4 DNA ligase, T7 DNA Ligase, E. coli DNA Ligase, Electro Ligase®, or the like. Conditions suitable for performing the ligation reaction will vary depending upon the type of ligase used. Information regarding such conditions is readily available.

In some embodiments, when a nucleic acid of the nucleic acid binding reagent is ligated to the nucleic acids of less than the desired length, the ends of the nucleic acid of the nucleic acid binding reagent and the ends of the nucleic acids of less than the desired length are designed to be compatible for ligation. For purposes of illustration, the nucleic acid of the nucleic acid binding reagent may be designed to include a dT overhang, and dA overhangs may be provided to the nucleic acids of the nucleic acid sample. In certain aspects, the dA overhangs are provided by end repair and dA tailing. Detailed guidance for how to provide such dA overhangs to nucleic acids of a nucleic acid sample, and enzymatically ligating the overhang-containing nucleic acids to a dT overhang-containing nucleic acid binding reagent, is provided in the Experimental section below.

In certain aspects, separating, using the affinity tag, the nucleic acids of less than the desired length bound to the nucleic acid binding reagent from the nucleic acids of the desired length not bound to the nucleic acid binding reagent, includes immobilizing on a solid support the nucleic acids of less than the desired length bound to the nucleic acid binding reagent. Suitable solid supports are described elsewhere herein and include, e.g., beads (e.g., magnetic beads, latex beads, or the like), planar supports, and the like. The solid support may include (e.g., have disposed thereon/attached thereto) a capture agent that binds to the affinity tag of the nucleic acid binding reagent.

A non-limiting example of the production of a size-selected nucleic acid library according to one embodiment is schematically illustrated in FIG. 1. In this particular example, the nucleic acid binding reagent is a double-stranded oligonucleotide having a dT overhang and desthiobiotin as the affinity tag. The nucleic acids of the nucleic acid sample are subjected to end repair and dA tailing, such that the oligonucleotide of the nucleic acid binding reagent and the nucleic acids have compatible ends for ligation. Shown at step 1 is the ligation of the desthiobiotinylated oligonucleotide to nucleic acids of the nucleic acid sample. The kinetics of ligation between a short strand and a short strand are much more rapid than between a short strand and a long strand. As shown at step 1, ligation of the desthiobiotinylated oligonucleotide to double-stranded DNA of the shortest lengths exhibits the most rapid ligation rate (shorter ligation time); ligation of the desthiobiotinylated oligonucleotide to double-stranded DNA of intermediate lengths exhibits an intermediate ligation rate (intermediate ligation time); and ligation of the desthiobiotinylated oligonucleotide to double-stranded DNA of the longest lengths exhibits the slowest ligation rate (longest ligation time).

As shown at step 2 of FIG. 1, in this example, once the ligation reaction has proceeded for a suitable period of time, the reaction mixture (or, e.g., a purified form thereof) is contacted with streptavidin-coated magnetic beads. The nucleic acid binding reagent (and any nucleic acid ligated thereto), is immobilized to the magnetic beads. The longer strands are substantially not ligated to the desthiobiotinylated oligonucleotide and therefore not retained on magnetic beads, while the short strands ligated to the desthiobiotinylated oligonucleotide are retained on magnetic beads. As indicated at step 3 of FIG. 1, by use of a magnet, the short strands can be selectively removed from solution leaving the size-selected longer strands (that is, the size-selected nucleic acid library) behind. The size-selected longer strands may be separated from the bead-short strand complexes by, e.g., aspirating the solution containing the size-selected longer strands and dispensing the solution into a suitable container, e.g., a tube, vial, well, etc.

In some embodiments, the methods of the present disclosure include subjecting polynucleotides of the size-selected nucleic acid library to a downstream application of interest. Non-limiting examples of such applications include, e.g., PCR amplification, southern analysis, northern analysis, nucleic acid sequencing, and/or the like.

In certain aspects, polynucleotides of the size-selected nucleic acid library are subjected to nucleic acid sequencing. The sequencing may be carried out on any suitable sequencing platform, including a Sanger sequencing platform, a high-throughput sequencing (HTS) (or "next-generation sequencing" ("NGS")) platform, or the like. HTS/NGS sequencing platforms of interest include, but are not limited to, a sequencing platform provided by Illumina® (e.g., the HiSeq™, MiSeq™ and/or Genome Analyzer™ sequencing systems); Oxford Nanopore™ Technologies (e.g., a MinION™, GridIONx5™, PromethION™, or SmidgION™ nanopore-based sequencing system), Ion Torrent™ (e.g., the Ion PGM™ and/or Ion Proton™ sequencing systems); Pacific Biosciences (e.g., the PACBIO RS II sequencing system); Life Technologies™ (e.g., a SOLiD sequencing system); Roche (e.g., the 454 GS FLX+ and/or GS Junior sequencing systems); or any other sequencing platform of interest. Detailed protocols for direct sequencing (e.g., by nanopore-based sequencing) or preparing compatible nucleic acid molecules for sequencing on a particular platform (e.g., by amplification, e.g., solid-phase amplification, or the like), sequencing the compatible molecules, and analyzing the sequencing data are available from the manufacturer of the sequencing platform of interest.

In certain aspects, when it is desirable to sequence polynucleotides of a size-selected nucleic acid library produced using the methods of the present disclosure, one or more sequencing adapters may be provided to the polynucleotides of the size-selected library. For example, one or more sequencing adapters (or subregions thereof) may be ligated, added by PCR (e.g., using primers including one or more sequencing adapters), etc., to one or both ends of the size-selected polynucleotides. By "sequencing adapter" is meant one or more nucleic acid domains that include at least a portion of a nucleic acid sequence (or complement thereof) utilized by a sequencing platform of interest, such as a sequencing platform provided by Illumina® (e.g., the HiSeq™, MiSeq™ and/or Genome Analyzer™ sequencing systems); Oxford Nanopore™ Technologies (e.g., a Min- ION™, GridIONx5™, PromethION™, or SmidgION™ nanopore-based sequencing system), Ion Torrent™ (e.g., the Ion PGM™ and/or Ion Proton™ sequencing systems); Pacific Biosciences (e.g., the PACBIO RS II sequencing system); Life Technologies™ (e.g., a SOLiD sequencing system); Roche (e.g., the 454 GS FLX+ and/or GS Junior sequencing systems); or any other sequencing platform of interest.

In certain aspects, the sequencing adapter is, or includes, a nucleic acid domain selected from: a domain (e.g., a "capture site" or "capture sequence") that specifically binds to a surface-attached sequencing platform oligonucleotide (e.g., the P5 or P7 oligonucleotides attached to the surface of a flow cell in an Illumina® sequencing system); a sequencing primer binding domain (e.g., a domain to which the Read 1 or Read 2 primers of the Illumina® platform may bind); a unique identifier (e.g., a barcode or other domain that uniquely identifies a nucleic acid of the library, and/or uniquely identifies the sample source of the library being sequenced to enable sample multiplexing by marking every molecule from a given sample with a specific barcode or "tag"); a barcode sequencing primer binding domain (a domain to which a primer used for sequencing a barcode binds); a molecular identification domain (e.g., a molecular index tag, such as a randomized tag of 4, 6, or other number of nucleotides) for uniquely marking molecules of interest, e.g., to determine expression levels based on the number of instances a unique tag is sequenced; a complement of any such domains; or any combination thereof. In certain aspects, a barcode domain (e.g., sample index tag) and a molecular identification domain (e.g., a molecular index tag) may be included in the same nucleic acid.

As noted above, polynucleotides of the size-selected nucleic acid library may be sequenced by nanopore-based sequencing. Any device/apparatus suitable for nanopore-based sequencing of polynucleotides of the size-selected nucleic acid library may be employed when practicing the subject methods. For example, a suitable device may include a chamber including an aqueous solution and a membrane that separates the chamber into two sections, the membrane including a nanopore formed therein. Electrical measurements may be made using single channel recording equipment such as that described, e.g., in Lieberman et al. (2010) *J. Am. Chem. Soc.* 132(50):17961-72; Stoddart et al. (2009) *PNAS* 106(19):7702-7; U.S. Pat. No. 9,481,908; and U.S. Patent Application Publication No. US2014/0051068; the disclosures of which are incorporated herein by reference in their entireties for all purposes. Alternatively, electrical measurements may be made using a multi-channel system, for example as described in U.S. Patent Application Publication No. US 2015/346149, the disclosure of which is incorporated herein by reference in its entirety for all purposes.

In nanopore sequencing, the nanopore serves as a biosensor and provides the sole passage through which an ionic solution on the cis side of the membrane contacts the ionic solution on the trans side. A constant voltage bias (trans side positive) produces an ionic current through the nanopore and drives ssDNA or ssRNA in the cis chamber through the pore to the trans chamber. A processive enzyme (e.g., a helicase, polymerase, nuclease, or the like) may be bound to the polynucleotide such that its step-wise movement controls and ratchets the nucleotides through the small-diameter nanopore, nucleobase by nucleobase. Because the ionic conductivity through the nanopore is sensitive to the presence of the nucleobase's mass and its associated electrical field, the ionic current levels through the nanopore reveal the sequence of nucleobases in the translocating strand. A patch clamp, a voltage clamp, or the like, may be employed.

Suitable conditions for measuring ionic currents through transmembrane pores (e.g., protein pores, solid state pores, etc.) are known in the art. Typically, a voltage is applied across the membrane and pore. The voltage used may be from +2 V to −2 V, e.g., from −400 mV to +400 mV. The voltage used may be in a range having a lower limit selected from −400 mV, −300 mV, −200 mV, −150 mV, −100 mV, −50 mV, −20 mV and 0 mV and an upper limit independently selected from +10 mV, +20 mV, +50 mV, +100 mV, +150 mV, +200 mV, +300 mV and +400 mV. The voltage may be in the range of from 100 mV to 240 mV, e.g., from 120 mV to 220 mV.

Nanopore-based sequencing methods are typically carried out in the presence of a suitable charge carrier, such as metal salts, for example alkali metal salts, halide salts, for example chloride salts, such as alkali metal chloride salt. Charge carriers may include ionic liquids or organic salts, for example tetramethyl ammonium chloride, trimethylphenyl ammonium chloride, phenyltrimethyl ammonium chloride, or I-ethyl-3-methyl imidazolium chloride. Generally, the salt is present in the aqueous solution in the chamber. Potassium chloride (KCl), sodium chloride (NaCl) or cesium chloride (CsCl) may be used, for example. The salt concentration may be at saturation. The salt concentration may be 3M or lower and is typically from 0.1 to 2.5 M, from 0.3 to 1.9 M, from 0.5 to 1.8 M, from 0.7 to 1.7 M, from 0.9 to 1.6 M, or from 1 M to 1.4 M. The salt concentration may be from 150 mM to 1 M. The methods are preferably carried out using a salt concentration of at least 0.3 M, such as at least 0.4 M, at least 0.5 M, at least 0.6 M, at least 0.8 M, at least 1.0 M, at least 1.5 M, at least 2.0 M, at least 2.5 M or at least 3.0 M. High salt concentrations provide a high signal to noise ratio and allow for currents indicative of the presence of a nucleotide to be identified against the background of normal current fluctuations.

In some embodiments, the rate at which a polynucleotide of the size-selected nucleic acid library is exposed to the nanopore is controlled using a processive enzyme. Non-limiting examples of processive enzymes that may be employed include polymerases (e.g., a phi29 or other suitable polymerase) and helicases, e.g., a Hel308 helicase, a RecD helicase, a TraI helicase, a TraI subgroup helicase, an XPD helicase, or the like. The polynucleotide may be bound by the processive enzyme (e.g., by binding of the processive enzyme to a recognition site present in a sequencing adapter located at an end of the polynucleotide), followed by the resulting complex being drawn to the nanopore, e.g., by a potential difference applied across the nanopore. In other aspects, the processive enzyme may be located at the nanopore (e.g., attached to or adjacent to the nanopore) such that the processive enzyme binds the polynucleotide upon arrival of the polynucleotide at the nanopore.

The nanopore may be present in a solid-state film, a biological membrane, or the like. In some embodiments, the nanopore is a solid-state nanopore. In other embodiments, the nanopore is a biological nanopore. The biological nanopore may be, e.g., an alpha-hemolysin-based nanopore, a *Mycobacterium smegmatis* porin A (MspA)-based nanopore, or the like.

Details for obtaining raw sequencing reads of nucleic acid molecules of interest using nanopores are described, e.g., in Feng et al. (2015) *Genomics, Proteomics & Bioinformatics* 13(1):4-16. Raw sequencing reads may be obtained using, e.g., a MinION™, GridIONx5™, PromethION™, or SmidgION™ nanopore-based sequencing system, available from Oxford Nanopore Technologies. Detailed design considerations and protocols for carrying out nanopore-based sequencing are provided with such systems.

Compositions

The present disclosure also provides compositions. The compositions find use in a variety of applications, including, e.g., practicing any of the methods of the present disclosure, including carrying out one or more of any of the steps described above in the Methods section of the present disclosure. As such, the compositions may include any of the nucleic acid binding reagents, affinity tags, covalent linking reagents, solid supports, other reagents, nucleic acid sample, etc. described above in the Methods section of the present disclosure, in any combination.

The compositions of the present disclosure may include the one or more components (e.g., any of the nucleic acid binding reagents, affinity tags, covalent linking reagents, solid supports, other reagents, nucleic acid sample, etc.) present in a container. Suitable containers include, but are not limited to, tubes, vials, and plates (e.g., a 96- or other-well plate).

In certain aspects, the compositions include the one or more components in a liquid medium. The liquid medium may be an aqueous liquid medium, such as water, a buffered solution, and the like. One or more additives such as a salt (e.g., NaCl, $MgCl_2$, KCl, $MgSO_4$), a buffering agent (a Tris buffer, N-(2-Hydroxyethyl)piperazine-N'-(2-ethanesulfonic acid) (HEPES), 2-(N-Morpholino)ethanesulfonic acid (MES), 2-(N-Morpholino)ethanesulfonic acid sodium salt (MES), 3-(N-Morpholino)propanesulfonic acid (MOPS), N-tris[Hydroxymethyl]methyl-3-aminopropanesulfonic acid (TAPS), etc.), a solubilizing agent, a detergent (e.g., a non-ionic detergent such as Tween-20, etc.), a nuclease inhibitor, glycerol, a chelating agent, and the like may be present in such compositions.

Kits

As summarized above, the present disclosure provides kits. The kits may include, e.g., any of the nucleic acid binding reagent, capture agents, solid supports, etc. having any of the features described hereinabove, in any desired combination. Kits of the present disclosure may further include any reagents, buffers, etc. useful for carrying out embodiments of the methods of the present disclosure.

According to some embodiments, a subject kit includes a nucleic acid binding reagent including an affinity tag, and instructions for using the affinity tag to produce a nucleic acid library that includes nucleic acids of a desired length, according to any embodiments of the methods of the present disclosure.

As will be appreciated, the kits of the present disclosure may include any of the components and features described above in the section relating to the subject methods, which are not reiterated in detail herein for purposes of brevity.

In certain aspects, the nucleic acid binding reagent of the kit includes a nucleic acid. In some embodiments, the nucleic acid of the nucleic acid binding reagent is an oligonucleotide. In some embodiments, a subject kit further includes a reagent for covalently linking the nucleic acid of the nucleic acid binding reagent to nucleic acids of a nucleic acid sample of less than a desired length. For example, a subject kit may further include a ligase, optionally with any buffers, co-factors, and/or the like useful for performing a ligation reaction.

In some embodiments, the nucleic acid binding reagent of the kit includes an affinity tag selected from biotin, a biotin analog (e.g., desthiobiotin), avidin, streptavidin, an aptamer, and a protein-interacting sequence.

In certain aspects, a subject kit further includes a solid support (e.g., bead, planar support, etc.) including a capture agent that binds to the affinity tag of the nucleic acid binding reagent.

Components of the kits may be present in separate containers, or multiple components may be present in a single container. A suitable container includes a single tube (e.g., vial), one or more wells of a plate (e.g., a 96-well plate, a 384-well plate, etc.), or the like.

The kits include instructions for using the affinity tag to produce a nucleic acid library that includes nucleic acids of a desired length, according to any embodiments of the methods of the present disclosure. The kit may further include instructions for adding one or more sequencing adapters to nucleic acids of the produced size-selected nucleic acid library. The kit may further include instructions for sequencing nucleic acids of the nucleic acid library, e.g., by next-generation sequencing (NGS) system (e.g., by nanopore-based sequencing).

The instructions of a subject kit may be recorded on a suitable recording medium. For example, the instructions may be printed on a substrate, such as paper or plastic, etc. As such, the instructions may be present in the kits as a package insert, in the labeling of the container of the kit or components thereof (i.e., associated with the packaging or sub-packaging) etc. In other embodiments, the instructions are present as an electronic storage data file present on a suitable computer readable storage medium, e.g., portable flash drive, DVD, CD-ROM, diskette, etc. In yet other embodiments, the actual instructions are not present in the kit, but means for obtaining the instructions from a remote source, e.g. via the internet, are provided. An example of this embodiment is a kit that includes a web address (or a code, e.g., a QR code, linking the user to a web address) where the instructions can be viewed and/or from which the instructions can be downloaded. As with the instructions, the means for obtaining the instructions is recorded on a suitable substrate.

Utility

The methods, compositions and kits of the present invention find use in a variety of contexts, including research, clinical, environmental, and other contexts.

As noted above, a difficulty in obtaining long sequencing reads of genomic DNA is delivery of only properly adapted unsheared long (>100 kb) DNA to the DNA sequencer. The presence of shorter DNA strands reduces the throughput for the desired long strand reads. One of the challenges in this process is removing unwanted shorter DNA strands in the sequencing library. The methods, compositions, and kits of the present disclosure obviate the need for expensive and time consuming size-selection methods, and contributes to the throughput of long read lengths needed for many sequencing applications, including those employing de novo assembly and scaffold building.

The following examples are offered by way of illustration and not by way of limitation.

EXPERIMENTAL

Example 1—Size-Selection of Long DNA Strands

Materials
1. 3M sodium acetate pH 5.2 100 ML S0296 3M Sodium Acetate pH 5.2 Sterile filtered. pH adjusted to 5.2 with Glacial Acetic acid. DNase RNase protease free. Size: 100 ml (Teknova Inc. Cat. No. S0296).

Figure 2:
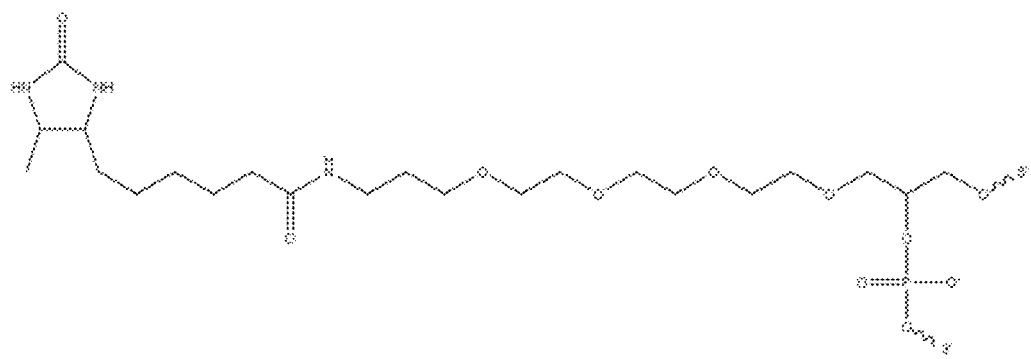
FIG. 2 shows the structure of 5' Desthiobiotin-TEG.

2. Dynabeads MyOne Streptavidin C1 Magnetic Beads (Life Technologies Corporation, Cat. No. 65001).
3. OmniPur® Phenol: Chloroform Phenol saturated with TE buffer for DNA isolation. (EMD Millipore Corporation Cat. No. 6805-100 ML).
4. Microcentrifuge Tubes; Eppendorf LoBind; 1.5 mL DNA; Genomic; PCR Clean; 250/Pk; 250/PK 022431021.
5. PCR Tubes 200 µl; 0.2 mL Thin Wall Tube in Strips of 8 With Individual Attached Dome Caps, Polypropylene, Natural, 120 Strips (960 Tubes and 960 Caps) per Pack, Cat. No. 1402-2900.
6. TE Buffer (Teknova Inc Cat No. T0224).
7. Quick-Load® 1 kb Extend DNA Ladder (NEB Cat. No. N3239S).
8. NEB Next Ultra II End Repair/dA-Tailing Module (NEB Cat. No. E7546S).
9. A DNA-HindIII Digest (NEB Cat. No. N3012S).
10. Blunt/TA Ligase Master Mix (NEB Cat. No. M0367S).
11. Lambda DNA (N6-methyladenine-free) (NEB Cat. No. N3013S).
12. Integrated DNA technology custom oligos:

(SEQ ID NO. 1)
/5Phos/GGGTTCAATCAAGGGTTCAATCAAGGGTTCAATCAAGGGTTC
AATCAAT (SEQ ID NO. 2)
/5deSBioTEG/TTGATTGAACCCTTGATTGAACCCTTGATTGAACCCT
TGATTGAACCC 5' Desthiobiotin-TEG (referred to above as 5deSBioTEG) has the structure shown in FIG. 2. TEG=triethylene glycol.

Methods

Preparation of Size-Selection Oligo
1. Custom Oligonucleotides supplied by IDT were resuspended in 50 mM NaCl, TE buffer (Teknova Inc. Cat No. T0224) at a concentration of 1 mM.
2. 4 µl of each oligo were combined in a lock top Eppendorf DNA low bind tube (Eppendorf Cat. No. 022431021) and placed in 600 ml water bath heated to 95° C. The water bath was immediately placed in a 4° C. refrigerator and allowed to cool to 4° C. over the course of 1 h.

End Repair and dA Tailing of 48 kb λ/HindIII λ Digest
1. The following were mixed together in a 200 µl PCR tube:
   a. 2 µl of 48 kb λ (~1 µg)
   b. 8 µl of HindIII λ digest (~4 µg)
   c. 40 µl of MilliQ nuclease free 18.2 Megohm water
   d. 7 µl of NEBNext Ultra II End Repair/dA-Tailing Module buffer
   e. 3 µl of NEBNext Ultra II End Repair/dA-Tailing Module enzyme mix
2. The mixture was incubated at room temp (20° C.) for 30 minutes.
3. The mixture was then brought to 100 µl final volume with MilliQ nuclease free 18.2 Megohm water and transferred to a 1.5 ml Eppendorf Low Bind tube, extracted 1× with phenol/chloroform, 2× with chloroform and precipitated by addition of 1/10 volume of 3 M NaOAc and 2.5 volumes of 100% ETOH.
   a. This material was examined using Pulsed Filed Gel Electrophoresis (PFGE).

Ligation of Custom Oligo to 48 kb λ/HindIII λ Digest
1. ~2 µg (~1 picomole of ligatable ends) of the 48 kb λ/HindIII λ digest mixture in 30 µl was combined with 1 µl and 5 µl of a 10 µM stock of the short DNA oligo with desthiobiotin tag.
2. 30 µl of Blunt/TA Ligase Master Mix, NEB Cat. No. M0367S were added to the mixture and the solution incubated for 20 minutes at 37° C.

Binding of Desthiobiotin-Labeled DNA to Streptavidin C1 Magnetic Beads
1. 50 µl of Dynabeads MyOne Streptavidin C1 Magnetic Beads-Life Technologies Corporation were added to the solution and allowed for binding material for 5 min.
2. The solution was placed on a magnetic tube holder and beads separated for bulk solution.
3. Bulk solution was transferred to a new tube This material was examined using Pulsed Field Gel Electrophoresis (PFGE).
4. DNA strands bound to Dynabeads MyOne Streptavidin C1 Magnetic Beads were eluted from the beads by incubation of beads with 50 µl of TE pH 8 buffer containing 1 mM biotin. This material was examined using Pulsed Field Gel Electrophoresis (PFGE).

Results

Figure 3:
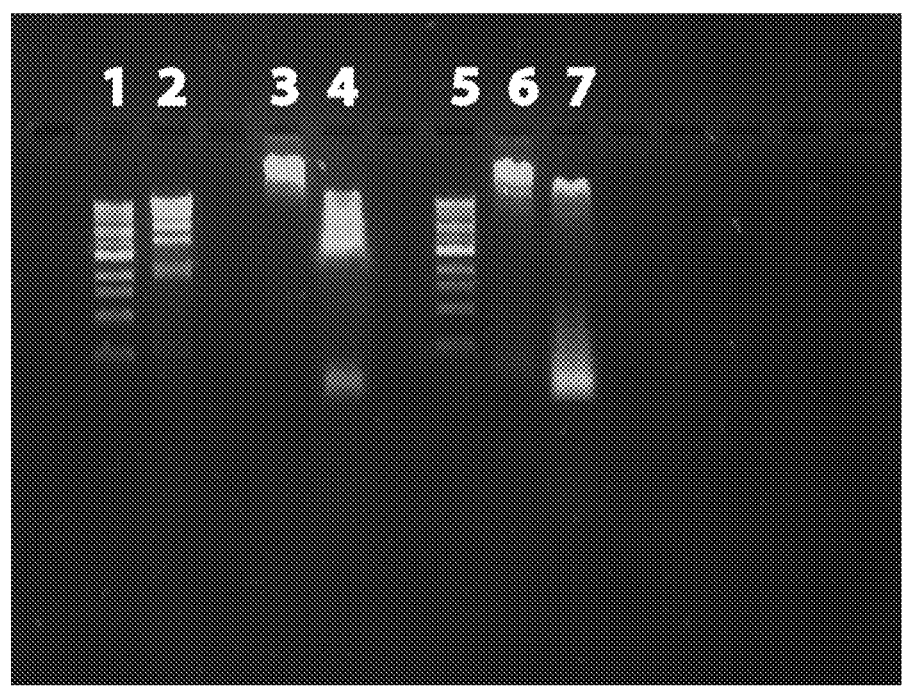
FIG. 3 shows pulsed field gel electrophoresis (PFGE) data demonstrating the production of a size-selected population of nucleic acids according to one embodiment of the present disclosure.

Shown in FIG. 3 are the results of pulsed gel electrophoresis of the starting DNA length mixture compared with the same mixture after size selection by ligation of a desthiobiotin tagged ds oligo and pull down of ligated short strands with streptavidin magnetic beads. Chromatography conditions used were an 0.8% agarose 0.5×TBE gel run for 3 hours in a BioRad CHEF Mapper® XA System Pulsed Field Electrophoresis (PFGE) unit. For PFGE, 180 degree FIGE mode with standard conditions (forward mode: 9 V, 90 seconds; reverse mode: 6 V, 30 seconds) was used and run for 2 hours. Descriptions of the lanes on the gel are provided below.

Lane 1: 10 µl of 1 Kb extended DNA ladder, NEB Cat No. N3239S with 0.5 kb, 1 kb, 1.5 kb, 2 kb, 3 kb, 4 kb, 5 kb, 6 kb, 8 kb, 10 kb, 15 kb, 20 kb, 48 kb DNA fragments.

Lane 2: ~2 µg mixture of 1 part 48 kb λ NEB Cat No. N3013S to 4 parts HindIII digest of and 48 kb λ NEB Cat No. N3012S. Sample had been end repaired/dA tailed with NEB Next Ultra II End Repair/dA-Tailing Module NEB Cat. No. E7546S, extracted with phenol/chloroform, precipitated with NaOAc and ETOH and then resuspended in TE buffer pH 8.0 at a concentration of ~100 ng/µl. Sizes of bands include—full length λ 48,502 bp and HindIII digest of λ—23,130 bp, 9,416 bp, 6,557 bp, 4,361 bp, 2,322 bp, 2,027 bp, 564 bp, 125 bp.

Lane 3: HindIII digest of 48 kb λ and 48 kb λ post ligation to 1 µl of ds 50 mer with desthiobiotin tag and subsequent incubation with streptavidin magnetic beads.

Lane 4: Biotin eluate from streptavidin beads after binding with desthiobiotin tagged DNA in lane 3.

Lane 5: 10 µl of 1 Kb extended DNA ladder, NEB Cat No. N3239S with 0.5 kb, 1 kb, 1.5 kb, 2 kb, 3 kb, 4 kb, 5 kb, 6 kb, 8 kb, 10 kb, 15 kb, 20 kb, 48 kb DNA fragments.

Lane 6: HindIII digest of 48 kb λ and 48 kb λ post ligation to 5 µl of ds 50mer with desthiobiotin tag and subsequent incubation with streptavidin magnetic beads.

Lane 7: Biotin eluate from streptavidin beads after binding with desthiobiotin tagged DNA in lane 6.

Lanes 4 and 7—containing DNA strands retained on the streptavidin magnetic beads after ligation to a short desthiobiotin-labeled oligo—are shorter than the corresponding DNA strands remaining in bulk phase solution in lanes 3 and 6, respectively. These results confirm ligation can serve as a size selection process for longer DNA strands.

Notwithstanding the appended claims, the disclosure is also defined by the following clauses:

1. A method for producing a size-selected nucleic acid library, comprising:
    contacting:
        a nucleic acid sample, and
        a nucleic acid binding reagent comprising an affinity tag,
        under conditions in which nucleic acids of less than a desired length are substantially bound to the nucleic acid binding reagent and nucleic acids of the desired length are substantially not bound to the nucleic acid binding reagent,
        wherein the conditions comprise the duration of the contacting, the concentration of the nucleic acid binding reagent, or both; and
    separating, using the affinity tag, the nucleic acids of less than the desired length bound to the nucleic acid binding reagent from the nucleic acids of the desired length not bound to the nucleic acid binding reagent, to produce a size-selected nucleic acid library.
2. The method according to Clause 1, wherein the conditions are such that 60% or more of the nucleic acids of less than the desired length are bound to the nucleic acid binding reagent during the separating.
3. The method according to Clause 1, wherein the conditions are such that 75% or more of the nucleic acids of less than the desired length are bound to the nucleic acid binding reagent during the separating.
4. The method according to any one of Clauses 1 to 3, wherein the conditions are such that 60% or more of the nucleic acids of the desired length are not bound to the nucleic acid binding reagent during the separating.
5. The method according to any one of Clauses 1 to 3, wherein the conditions are such that 75% or more of the nucleic acids of the desired length are not bound to the nucleic acid binding reagent during the separating.
6. The method according to any one of Clauses 1 to 5, wherein the nucleic acid sample comprises deoxyribonucleic acid (DNA).
7. The method according to Clause 6, wherein the nucleic acid sample is a genomic DNA sample.
8. The method according to Clause 6 or Clause 7, wherein nucleic acids of the desired length are 10 kb or greater in length.
9. The method according to Clause 6 or Clause 7, wherein nucleic acids of the desired length are 25 kb or greater in length.
10. The method according to Clause 6 or Clause 7, wherein nucleic acids of the desired length are 50 kb or greater in length.
11. The method according to Clause 6 or Clause 7, wherein nucleic acids of the desired length are 100 kb or greater in length.
12. The method according to Clause 6, wherein the nucleic acid sample is a complementary DNA (cDNA) sample.
13. The method according to any one of Clauses 1 to 5, wherein the nucleic acid sample comprises ribonucleic acid (RNA).
14. The method according to Clause 13, wherein nucleic acids of the desired length are messenger RNAs (mRNAs).
15. The method according to any one of Clauses 12 to 14, wherein nucleic acids of the desired length are 500 base pairs (bp) or greater in length.
16. The method according to any one of Clauses 1 to 15, wherein the nucleic acid binding reagent comprises a nucleic acid.
17. The method according to Clauses 16, wherein the nucleic acid of the nucleic acid binding reagent is an oligonucleotide.
18. The method according to Clause 16 or Clause 17, wherein binding of nucleic acids of less than the desired length to the nucleic acid binding reagent comprises covalently linking the nucleic acids of less than the desired length to the nucleic acid of the nucleic acid binding reagent.
19. The method according to Clause 18, wherein the covalently linking is by enzymatic ligation.
20. The method according to any one of Clauses 1 to 19, wherein the affinity tag is selected from the group consisting of: biotin, a biotin analog, avidin, streptavidin, an aptamer, and a protein-interacting sequence.
21. The method according to any one of Clauses 1 to 19, wherein the affinity tag comprises biotin or a biotin analog.
22. The method according to Clause 21, wherein the affinity tag is desthiobiotin.
23. The method according to any one of Clauses 1 to 22, wherein the separating comprises immobilizing on a solid support the nucleic acids of less than the desired length bound to the nucleic acid binding reagent.
24. The method according to Clause 23, wherein the solid support comprises a capture agent that binds to the affinity tag of the nucleic acid binding reagent.
25. The method according to any one of Clauses 1 to 24, further comprising sequencing the nucleic acids of the size-selected nucleic acid library.
26. The method according to Clause 25, wherein the sequencing is by next-generation sequencing (NGS).
27. The method according to Clause 26, wherein the next-generation sequencing is nanopore-based sequencing.
28. A kit, comprising:
    a nucleic acid binding reagent comprising an affinity tag; and
    instructions for using the affinity tag to produce a size-selected nucleic acid library according to the method of any one of Clauses 1 to 27.
29. The kit of Clause 28, wherein the nucleic acid binding reagent comprises a nucleic acid.
30. The kit of Clause 29, wherein the nucleic acid of the nucleic acid binding reagent is an oligonucleotide.
31. The kit of Clause 29 or Clause 30, further comprising a reagent for covalently linking the nucleic acid of the nucleic acid binding reagent to nucleic acids of a nucleic acid sample of less than a desired length.
32. The kit of Clause 31, wherein the reagent is a ligase.

33. The kit of any one of Clauses 28 to 32, wherein the affinity tag is selected from the group consisting of: biotin, a biotin analog, avidin, streptavidin, an aptamer, and a protein-interacting sequence.
34. The kit of any one of Clauses 28 to 32, wherein the affinity tag comprises biotin or a biotin analog.
35. The kit of Clause 34, wherein the affinity tag is desthiobiotin.
36. The kit of any one of Clauses 28 to 35, further comprising a solid support comprising a capture agent that binds to the affinity tag.
37. The kit of any one of Clauses 28 to 36, wherein the instructions further comprise instructions for sequencing nucleic acids of the nucleic acid library.
38. The kit of Clause 37, wherein the sequencing is by next-generation sequencing (NGS).
39. The kit of Clause 38, wherein the next-generation sequencing is nanopore-based sequencing.

Accordingly, the preceding merely illustrates the principles of the present disclosure. It will be appreciated that those skilled in the art will be able to devise various arrangements which, although not explicitly described or shown herein, embody the principles of the invention and are included within its spirit and scope. Furthermore, all examples and conditional language recited herein are principally intended to aid the reader in understanding the principles of the invention and the concepts contributed by the inventors to furthering the art, and are to be construed as being without limitation to such specifically recited examples and conditions. Moreover, all statements herein reciting principles, aspects, and embodiments of the invention as well as specific examples thereof, are intended to encompass both structural and functional equivalents thereof. Additionally, it is intended that such equivalents include both currently known equivalents and equivalents developed in the future, i.e., any elements developed that perform the same function, regardless of structure. The scope of the present invention, therefore, is not intended to be limited to the exemplary embodiments shown and described herein.

What is claimed is:

1. A method for producing a size-selected nucleic acid library, comprising:
    contacting in a solution:
        a nucleic acid sample comprising double-stranded deoxyribonucleic acid (DNA) of 10 kilobases (kb) or greater in length and double-stranded DNA of less than 10 kb in length, with
        a tagged oligonucleotide, the tagged oligonucleotide comprising an affinity tag; and a nucleic acid ligase,
        for a duration such that 60% or more of the double-stranded DNA of less than 10 kb in length is ligated to the tagged oligonucleotide and 60% or more of the double-stranded DNA of 10 kb or greater in length is not ligated to the tagged oligonucleotide; and
    removing from the solution, using the affinity tag, the 60% or more of the double-stranded DNA of less than 10 kb in length ligated to the tagged oligonucleotide,
    to produce a size-selected nucleic acid library comprising the 60% or more of the double-stranded DNA of 10 kb or greater in length.

2. The method according to claim 1, wherein the nucleic acid sample is a genomic DNA sample.
3. The method according to claim 1, wherein the nucleic acid sample comprises messenger RNAs (mRNAs).
4. The method according to claim 1, wherein the affinity tag is selected from the group consisting of: biotin, desthiobiotin, avidin, streptavidin, an aptamer, and a protein-interacting sequence.
5. The method according to claim 1, wherein the affinity tag comprises biotin.
6. The method according to claim 1, wherein the affinity tag comprises desthiobiotin.
7. The method according to claim 1, wherein the removing step comprises immobilizing on a solid support the 60% or more of the double-stranded DNA of less than 10 kb ligated to the tagged oligonucleotide.
8. The method according to claim 7, wherein the solid support comprises a capture agent that binds to the affinity tag of the tapped oligonucleotide.

SEQUENCE LISTING

```
<160> NUMBER OF SEQ ID NOS: 2

<210> SEQ ID NO 1
<211> LENGTH: 49
<212> TYPE: DNA
<213> ORGANISM: Artificial Sequence
<220> FEATURE:
<223> OTHER INFORMATION: Sythetic nucleotide sequence

<400> SEQUENCE: 1
gggttcaatc aagggttcaa tcaagggttc aatcaagggt tcaatcaat          49

<210> SEQ ID NO 2
<211> LENGTH: 48
<212> TYPE: DNA
<213> ORGANISM: Artificial Sequence
<220> FEATURE:
<223> OTHER INFORMATION: synthetic nucleotide sequence

<400> SEQUENCE: 2
ttgattgaac ccttgattga acccttgatt gaacccttga ttgaaccc            48
```

9. The method according to claim 1, further comprising sequencing the nucleic acids of the size-selected nucleic acid library.

10. The method according to claim 9, wherein the sequencing is by nanopore sequencing.

11. The method according to claim 1, wherein the 60% or more of the double-stranded DNA of less than 10 kb in length is ligated to the tagged oligonucleotide via blunt-end ligation.

* * * * *